United States Patent
Lenes et al.

(10) Patent No.: US 10,436,879 B2
(45) Date of Patent: Oct. 8, 2019

(54) SATELLITE METHOD AND SYSTEM FOR DETECTING A FLOATING LAYER ON A SEA SURFACE TO BE MONITORED

(71) Applicant: ELECTRICITE DE FRANCE, Paris (FR)

(72) Inventors: Arnaud Lenes, Londres (GB); Jean-Benoit Ritz, Londres (GB)

(73) Assignee: ELECTRICITE DE FRANCE, Paris (FR)

( * ) Notice: Subject to any disclaimer, the term of this patent is extended or adjusted under 35 U.S.C. 154(b) by 341 days.

(21) Appl. No.: 15/310,888

(22) PCT Filed: May 12, 2015

(86) PCT No.: PCT/FR2015/051246
§ 371 (c)(1),
(2) Date: Nov. 14, 2016

(87) PCT Pub. No.: WO2015/173510
PCT Pub. Date: Nov. 19, 2015

(65) Prior Publication Data
US 2017/0090017 A1    Mar. 30, 2017

(30) Foreign Application Priority Data
May 14, 2014 (FR) .................... 14 54267

(51) Int. Cl.
*G01S 7/41* (2006.01)
*G01N 33/18* (2006.01)
*G01S 13/88* (2006.01)
*G01S 13/95* (2006.01)

(52) U.S. Cl.
CPC .......... *G01S 7/411* (2013.01); *G01N 33/1833* (2013.01); *G01S 7/415* (2013.01);
(Continued)

(58) Field of Classification Search
CPC .......... G01S 7/415; G01S 7/411; G01S 13/88; G01S 13/882; G01S 13/89;
(Continued)

(56) References Cited

U.S. PATENT DOCUMENTS 5,633,644 A * 5/1997 Schussler ............... G01S 13/91
   342/455
7,456,780 B1 * 11/2008 Garren .................... G01S 7/415
   342/115

(Continued)

OTHER PUBLICATIONS

Antunes Pelizzari, "Oil Spill Detection Using SAR Images," Thesis, Institute Superior Tecnico, Feb. 2011, retrieved from internet website: http://www.lx.it.pt/~bioucas/files/PhD_sonia_oil_detection.pdf on Jan. 9, 2015, 140 pages.

(Continued)

*Primary Examiner* — Bernarr E Gregory
*Assistant Examiner* — Daniel P Malley, Sr.
(74) *Attorney, Agent, or Firm* — Drinker Biddle & Reath LLP (57) ABSTRACT

A method and system for detecting a floating layer on a surveillance area of the sea surface, a site of interest being placed in or around the surveillance area. The method comprises the following steps: a) satellite measurement of a radar feedback return, the radar signal being emitted by a satellite toward the sea surface of the surveillance area; b) recognition of at least one swell profile of the sea surface in accordance with the satellite measurements; c) identification of the fluid properties corresponding to the recognized swell profiles; and d) emission of a warning when the fluid properties identified for one of the recognized profiles correspond to a sea surface that includes undesirable elements for the site of interest.

11 Claims, 5 Drawing Sheets

(52) U.S. Cl.
CPC .............. *G01S 13/88* (2013.01); *G01S 13/882* (2013.01); *G01S 13/955* (2013.01); *Y02A 20/206* (2018.01); *Y02A 90/18* (2018.01)

(58) Field of Classification Search
CPC ... G01S 13/9035; G01S 13/955; G01N 33/00; G01N 33/18; G01N 33/1833; Y02A 20/20; Y02A 20/206; Y02A 90/17; Y02A 90/18
See application file for complete search history.

(56) References Cited

U.S. PATENT DOCUMENTS

| | | | | |
|---|---|---|---|---|
| 2003/0072004 | A1* | 4/2003 | Huang | G01N 21/45 356/450 |
| 2004/0257264 | A1* | 12/2004 | Moeller-Jensen | G01N 33/1833 342/52 |
| 2014/0159938 | A1* | 6/2014 | Shipley | G01V 3/12 342/22 |
| 2015/0051883 | A1* | 2/2015 | Mano | F17D 5/02 703/2 |

OTHER PUBLICATIONS

Belov et al., "Application of Ground-based and Air/Spaceborne Radars for Oil Spill Detection in Sea Areas," Telecommunications and Radio Engineering, Scripta Technica, Inc., New York, NY, US, Jan. 1, 1997, vol. 51(1), pp. 1-8.

Brekke et al., "Oil spill detection by satellite remote sensing," Remote Sensing of Environment, Elsevier, Mar. 15, 2005, vol. 95(1), pp. 1-13.

Dehqanzada et al., "Secrets for Sale: How Commercial Satellite Imagery Will Change the World," Carnegie Endowment for International Peace, Jan. 2000, retrieved from internet website: http://carnegieendowment.org/files/FINALreport.pdf on Jan. 9, 2015, 55 pages.

Fingas et al., "Review of oil spill remote sensing," Marine Pollution Bulletin, Elsevier, Apr. 20, 2014, vol. 83(1), pp. 9-23.

Fujita et al., "SIR-B Experiments in Japan: Sensor Calibration and Oil Pollution Detection Over Ocean," IEEE Transactions on Geoscience and Remote Sensing, IEEE Service Center, Piscataway, NJ, US, Jul. 1, 1986, vol. 44(4), pp. 567-574.

Miller et al., "Objectives and Capabilities of the Skylab S-193 Altimeter Experiment," IEEE Transactions on Geoscience Electronics, IEEE, US, Jan. 1, 1972, vol. 1(1), pp. 73-79.

Solberg et al., "Oil Spill Detection in Radarsat and Envisat SAR Images," EEE Transactions on Geoscience and Remote Sensing, IEEE Service Center, Piscataway, NJ, US, Mar. 1, 2007, vol. 45(3), pp. 746-755.

Vogt et al., "Monitoring of marine oil spills from SAR satellite data," Proceedings of SPIE, SPIE, Nov. 16, 2004, vol. 5569, pp. 209-219.

* cited by examiner

# SATELLITE METHOD AND SYSTEM FOR DETECTING A FLOATING LAYER ON A SEA SURFACE TO BE MONITORED

CROSS-REFERENCE TO RELATED APPLICATIONS

This application is the U.S. national phase of the International Patent Application No. PCT/FR2015/051246 filed May 12, 2015, which claims the benefit of French Application No. 14 54267 filed May 14, 2014, the entire content of which is incorporated herein by reference.

TECHNICAL FIELD

The invention relates to the field of detecting a floating layer on a water surface, in particular a sea surface near the coastline. The proposed detection of a floating layer aims in particular to anticipate the risks and threats inherent in the presence of a floating layer near seaside facilities such as a nuclear power plant.

BACKGROUND

The cooling system of an electric power plant installed on the coast (such as a thermal power station) is generally supplied with water from the sea. Drum screens may be used to filter the seawater supplied to the cooling system pumps.

However, floating layers of organisms (a cluster of jellyfish for example) or of pollution (typically an oil slick or a layer of debris) can form on the sea surface. The presence of such floating layers can congest the filtering drum screens. Beyond a certain amount of congestion, the clogging of the drums prevents the pumps from functioning normally, which can result in the loss of the heat sink for the plant.

It is generally necessary to shut down the cooling system in order to clear the drum screens, which means a simultaneous shutdown of electric power production by the plant.

In order to prevent drum screen clogging and to avoid the resulting shutdown of power production, there is a need to anticipate the possibility of drum screen clogging, in particular by detecting the presence of floating layers near the plant.

Currently, aerial surveillance flyovers are sometimes established in order to monitor the sea surfaces around a plant and to detect the possible presence of any floating layers.

However, this aerial surveillance is limited both temporally and spatially, and must be carried out during the day. As a result, this monitoring technique is exclusively used for the management of already reported crisis situations.

There is therefore a need for a technique enabling preventive detection of floating layers which are a potential threat to a site of interest such as a thermal power station.

Furthermore, the behavior of floating layers on the water surface varies with their composition. For example, a layer of obstructing organisms (such as jellyfish or algae) does not behave in the same manner as an oil slick, and these do not present the same risk of clogging the drum screens of the plant.

There is therefore also a need to characterize the composition of floating layers detected near the plant, in order to better anticipate the potential for clogging.

The invention improves the situation in this regard.

SUMMARY

The aim of the invention is to overcome the above disadvantages and to satisfy the stated needs, in particular by using satellite radar measurements to detect layers on the water surface and, from these satellite measurements, to interpret the fluid properties of the detected layers in order to determine their composition.

To this end, a first aspect of the invention relates to a method for detecting a floating layer on a surveillance area of a sea surface, a site of interest being located in or at the edge of the surveillance area. The method comprises at least the steps of:

a) satellite measurement of a returned radar signal, the radar signal being transmitted by a satellite toward the sea surface of the surveillance area;

b) recognition of at least one swell profile of the sea surface, based on the satellite measurements;

c) identification of the fluid properties corresponding to the recognized swell profiles; and d) emission of a warning when the fluid properties identified for one of the recognized profiles correspond to a sea surface comprising elements that are undesirable for the site of interest.

"At the edge" is understood to mean a location of a site of interest that is positioned within an area extending around the surveillance area, for example for a distance of up to a hundred kilometers.

The use of satellite measurements allows covering large areas in an almost continuous manner, due to the regular passage of satellites over the surveillance area.

In addition, the radar measurements used allow being free from the presence of cloud cover over the surveillance area and can be carried out day or night (clouds and light conditions have no impact on the detection levels of satellite radar measurements).

The satellite measurements allow determining:

altimetric variations of the sea surface, based on the wavelength and amplitude of the measured return signal levels, and/or variations in the roughness of the sea surface, based on average values of the measured return signal levels.

"Roughness" of the sea surface is understood to mean a slight variation in the contours of the sea surface, which can manifest in the form of wavelets or ripples.

These variations in altimetry and in roughness allow differentiating the swell characteristics of the sea surface. The portions of the surveillance area which have similar swell characteristics correspond to a swell profile for this area. Typically, portions of the surveillance area having high altimetric variations can correspond to a first profile, while a portion of the surveillance area having low altimetric variations can correspond to a second profile. Based on the identified swell profiles in the surveillance area, a floating layer can be recognized as an area having a different swell profile than the surrounding swell.

In addition, the satellite measurements can be interpreted to determine the fluid properties of the sea surface. In the current case, the fluid properties of the sea surface can be evaluated based on the behavior of the swell at the water surface, in other words based on the swell characteristics of the swell profile or profiles identified within the surveillance area. The determined fluid properties can be used to characterize the composition of the water surface and estimate the concentration of elements that are undesirable for the site of interest.

When the swell characteristics of an identified swell profile correspond to a sea surface comprising elements that are undesirable for the site of interest, a warning may be issued concerning the possibility of drum screen clogging for example. It is thus possible to implement preventive measures to avoid such obstruction.

Typically, the site of interest may be a thermal power station such as a nuclear power plant located on the coast, an oil rig, a desalination plant, an aquaculture farm, or some other site.

The elements that are undesirable for the site of interest may be in the form of:
- marine organisms such as jellyfish, ctenophora, algae, or fish;
- pollution such as crude oil or debris;
- or other elements.

Advantageously, the dimensions of the surveillance area are based on parameters among the following:
- speeds of the ocean currents;
- a tidal coefficient;
- weather conditions;
- a predetermined surveillance frequency; and
- frequency at which the satellite passes over the surveillance area.

For example, the size of the surveillance area may be:
- large (between 10 and 100 km2) if the satellite passes over the surveillance area infrequently (typically once a day) and the wind speed is high,
- small (1 to 10 km2) if the satellite passes over the surveillance area frequently (for example every quarter hour) and the wind speed is low.

Thus, the surveillance area can be adjusted to the conditions in which the surveillance occurs, which limits the potential measurement disruptions that are inherent to the conditions mentioned above. On a purely qualitative basis, the dimensions of the surveillance area are adjusted to the weather conditions. The quality and precision of the floating layer detection can thus be further improved.

According to a particularly advantageous embodiment, in step b), distinctive boundaries of the swell profile may further be recognized in the surveillance area, distinctive boundaries corresponding to pronounced localized variations in the levels of the satellite measurements.

The identified distinctive boundaries define areas where the swell characteristics are greatly modified, which is generally found at the transition between two different swell profiles. Abrupt changes in swell characteristics reflect a change in fluid properties (or bathymetry), and therefore potentially a local change in the composition of the sea surface. Recognized distinctive boundaries thus allow more clearly delimiting the swell profiles of the surveillance area.

In addition, the recognized distinctive boundaries may be compared to a bathymetric mapping of the surveillance area.

In this manner, it is possible to identify changes to the swell caused by bathymetric refraction and to isolate them so they do not skew the recognition of distinctive boundaries of swell profiles. An abrupt change of swell characteristics that is not located in an area of pronounced change in bathymetry cannot be associated with bathymetric refraction. This change can therefore be associated with a change of composition of the sea surface, indicating the potential presence of a floating layer.

Any layer detection errors caused by shallow seas are thus avoided.

In a first advantageous embodiment, the at least one recognized swell profile corresponds to a set of measurements of substantially the same level, the set of measurements being bounded at least in part by the recognized distinctive boundaries.

"Substantially the same level" is understood to mean a set of measurements of the same level or varying around the same average value for the detection level.

Measurements of substantially the same level may correspond to a water surface having the same roughness. In addition, when the set of measurements is bounded at least in part by the recognized distinctive boundaries, the set of measurements may correspond to a swell profile characterized by this same roughness.

As an illustrative example, a sea surface in the presence of an oil slick is generally smoother (less rough) than the surface of the surrounding water. The oil slick is usually surrounded by abrupt variations in the swell at its edges, which may manifest as a rapid damping of the surrounding swell at the periphery of the slick or as swell amplitudes that differ from the identified profiles in the surveillance area.

Advantageously, at least the following can be recognized in the surveillance area:
- a first swell profile based on a set of measurements of substantially a same first level,
- a second swell profile based on a set of measurements of substantially a same second level.

The first and second levels can be compared. The first or the second swell profile corresponding to the lower of the compared levels can be associated with the fluid properties of a sea surface having elements that are undesirable for the site of interest.

According to this embodiment, the first and second levels correspond to different roughnesses (surface wavelets of the swell) of the sea surface. Areas of high roughness return a strong radar echo to the satellite, and conversely, areas of low roughness reflect very little radar signal to the satellite (phenomenon of reflection in a direction at an angle to the sea surface which is equivalent to the angle of incidence of the radar signal sent).

Undesirable elements, such as oil slicks, can alter the roughness of the sea surface. Typically, when crude oil is present, the sea surface is composed of two immiscible fluids where the lighter one (the oil) floats on top. The oil slick formed on the surface has a pronounced effect on the viscosity and surface tension and heavily impacts waves of small wavelength and amplitude, thus modifying the apparent roughness at the sea surface. Distinctive changes in roughness then appear on the water surface between:
- the oil slick which is of low roughness, and
- the surface of the surrounding sea which is of a higher roughness.

The lower of the first and second levels measured by the satellite can therefore correspond to a sea surface which may include elements that are undesirable for the site of interest, such as an oil slick.

According to a second advantageous embodiment, the at least one recognized swell profile corresponds to a set of measurements for which the level varies by a same wavelength and a same amplitude, the set of measurements being bounded at least in part by the recognized distinctive boundaries.

A set of measurements, defined by the recognized distinctive boundaries and for which the measurement levels vary by a same wavelength and a same amplitude, may characterize a swell profile. A sea surface generally behaves uniformly in areas exposed to the same weather phenomena, in particular with a same wavelength and a same swell amplitude.

Advantageously, in step c), the fluid properties of the at least one recognized swell profile are identified by:

determining a volume fraction as a function of:
a damping coefficient of amplitude of the swell at the distinctive boundaries,
a number of waves at the distinctive boundaries, determined from the wavelength of the recognized swell profile,
identifying the fraction among the predefined volume fractions that is closest to the determined volume fraction, the predefined volume fractions being associated with predetermined fluid properties; and
associating the recognized swell profile with the predetermined fluid properties of the predefined volume fraction identified as being closest to the determined volume fraction.

Sea waves are damped when they encounter layers of undesirable elements such as clusters of clogging organisms (jellyfish, algae, or other), and the damping behavior allows determining a volume fraction of the sea surface which is dependent on wave damping in the detected swell profile.

The determined volume fraction can be compared to a volume fraction database. The volume fractions stored in the database may be fractions predetermined for different clogging organisms and for different climatic and weather conditions. The clogging organisms stored in this database may be specified with different volume fractions indicating the fluid properties they induce on the water surface, in particular their behavior according to season, weather conditions, light conditions, water temperature, or other, to allow recognizing them under the conditions in which the measurements are obtained.

For example, depending on whether the measurements are obtained during the day or at night, a clogging organism such as a jellyfish does not behave in the same manner. Such variations in behavior have an impact on the swell and can be identified by matching the fraction derived from the measurements with those of the database.

In addition, the predefined volume fractions may correspond to volume fractions observed in known weather conditions, for sea surfaces having identified floating bodies.

A database of volume fractions can thus be constructed in advance for subsequently identifying undesirable elements detected in the surveillance area.

In addition, the volume fraction determined for a swell profile may also take into account the effects of the surface tension of the corresponding sea surface.

Advantageously, the method further comprises a step of determining movement of a swell profile corresponding to a sea surface comprising elements that are undesirable for the site of interest, the movement determination being based on pre-established hydrodynamic models of the surveillance area or on hydrodynamic models from sources of information about the hydrodynamic conditions of the surveillance area.

It is thus possible to predict the movement of a floating layer posing a threat to the site of interest and to anticipate measures to be taken, for example to protect the cooling system of a thermal power station. Management and protection of the heat sink of such a station are therefore improved, which allows warning of the possibility of drum screen clogging and avoiding the resulting shutdown of power production.

In a second aspect, the invention provides a system for detecting a floating layer in a surveillance area of a sea surface, a site of interest being located in or at the edge of the surveillance area.

The system comprises at least:
a satellite configured to:
transmit a radar signal toward the sea surface of the surveillance area;
measure a return signal of the transmitted radar signal;
communicate data concerning the measurement levels of the measured return signals;
a management unit comprising:
a communication interface configured to receive the data communicated by the satellite, and
a data processing unit configured to implement the steps of the detection method according to the aforementioned method.

The system may further comprise a database configured for storing data relating to:
predetermined volume fractions corresponding to volume fractions observed in known weather conditions, for sea surfaces having identified floating bodies; and/or
a bathymetric mapping of the surveillance area.

In addition, the site of interest may be a power generation facility such as a nuclear power plant or tidal turbines.

The present invention also relates to a computer program comprising instructions for implementing the method described above, when the program is executed by a data processing unit such as a processor.

This program may use any programming language (for example an object-oriented language or some other language), and may be in the form of interpretable source code, partially compiled code, or fully compiled code.

Figure 7:
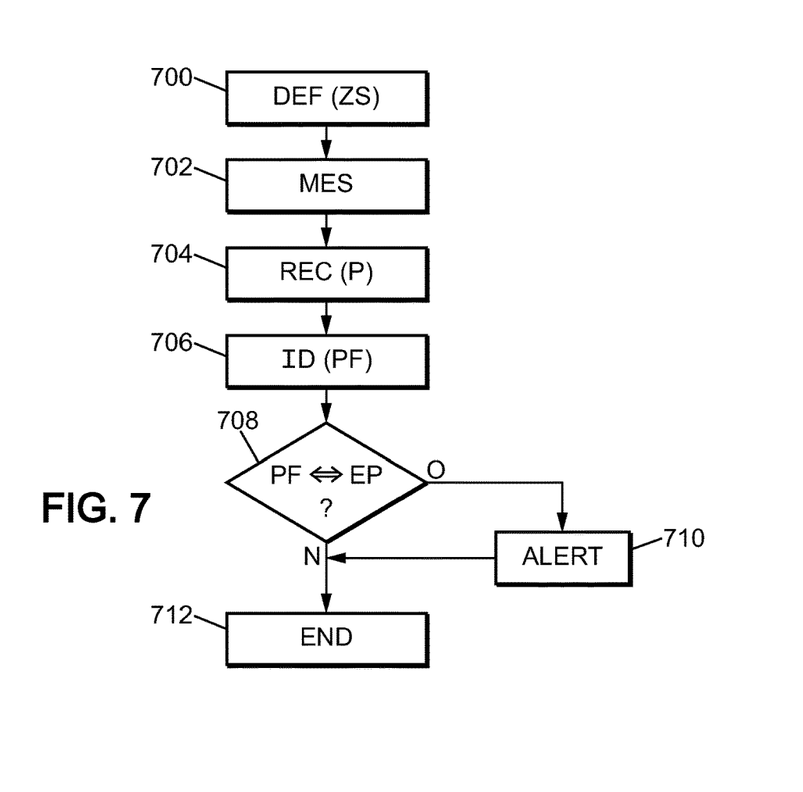
FIG. 7 is a flowchart composed of an exemplary sequence of steps in the detection method according to the invention.

FIG. 7, described in detail below, can serve as a flowchart of the general algorithm of such a computer program.

BRIEF DESCRIPTION OF THE DRAWINGS

Other features and advantages of the invention will become apparent from the following detailed description and from the attached figures in which.

For clarity, the dimensions of the various elements represented in these figures are not in proportion to their actual dimensions. In the figures, identical references correspond to identical elements for the various embodiments described.

DETAILED DESCRIPTION

Figure 1A:
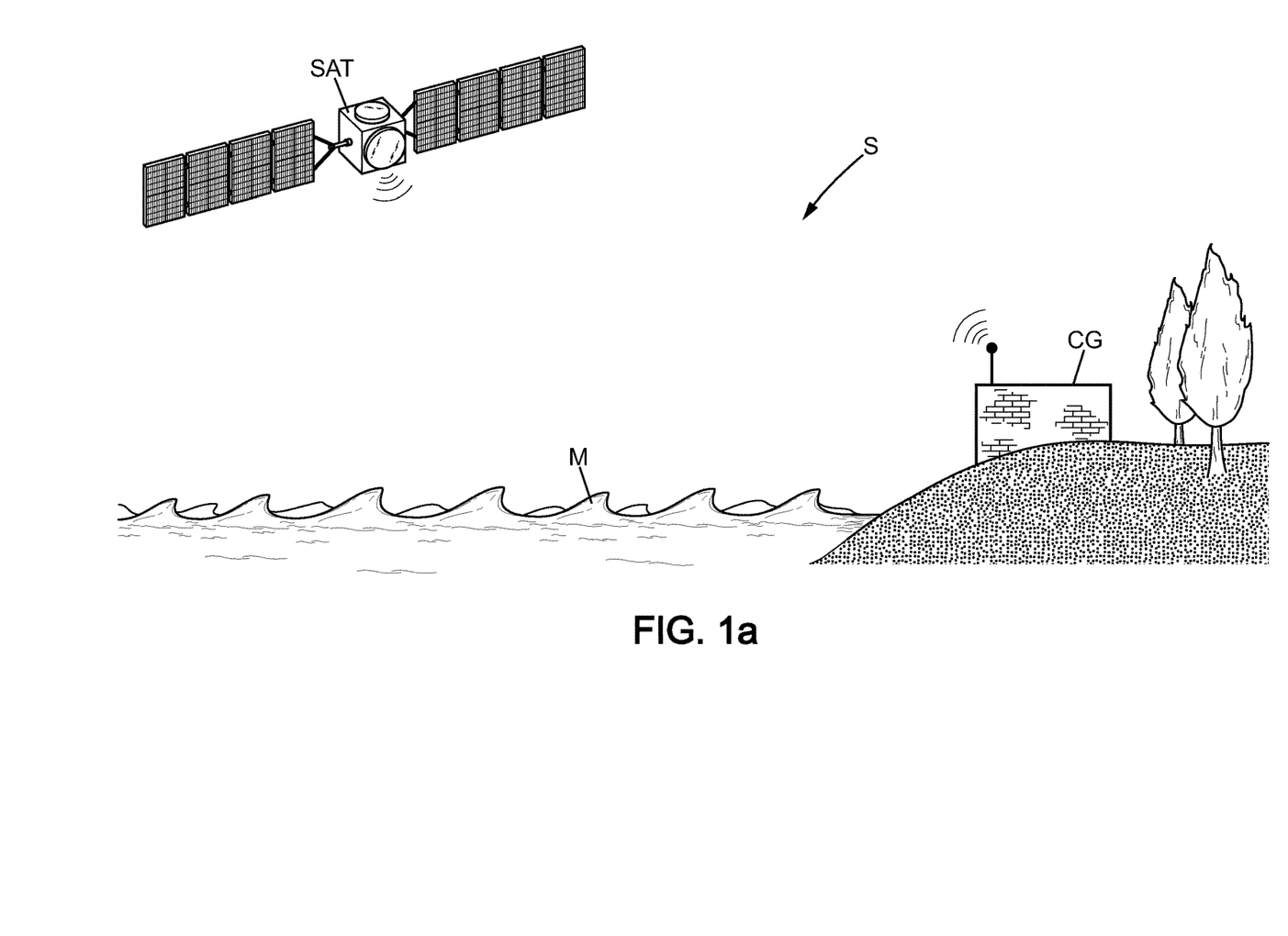
FIGS. 1a and 1b illustrate an example of a system for detecting a floating layer according to the invention.

We first refer to FIG. 1a which illustrates an embodiment of the system for detecting a floating layer according to the invention.

In this example, the system S comprises a satellite SAT configured to:

send a radar signal toward the sea M, and in particular toward a sea surface to be monitored;

measure a return signal of the transmitted radar signal;

communicate data concerning the measurement levels of the measured return signals.

To this end, the satellite SAT may comprise a radar altimeter transmitter operating in a non-visible frequency range, emitting signals for example within a frequency between 12 and 18 GHz. The accuracy of the altimetric measurements is preferably 10 centimeters vertically and 1 meter horizontally in order to correctly detect the different swells at the water surface.

In addition, the satellite SAT may include a communication module for sending measurement data to a management center CG. The center CG processes the data sent by the satellite in order to detect floating layers on the surface of the sea M.

In this embodiment, the center CG is a separate entity. However, in other possible embodiments, the center CG may be directly embedded in the satellite or installed in a power plant.

Figure 1B:
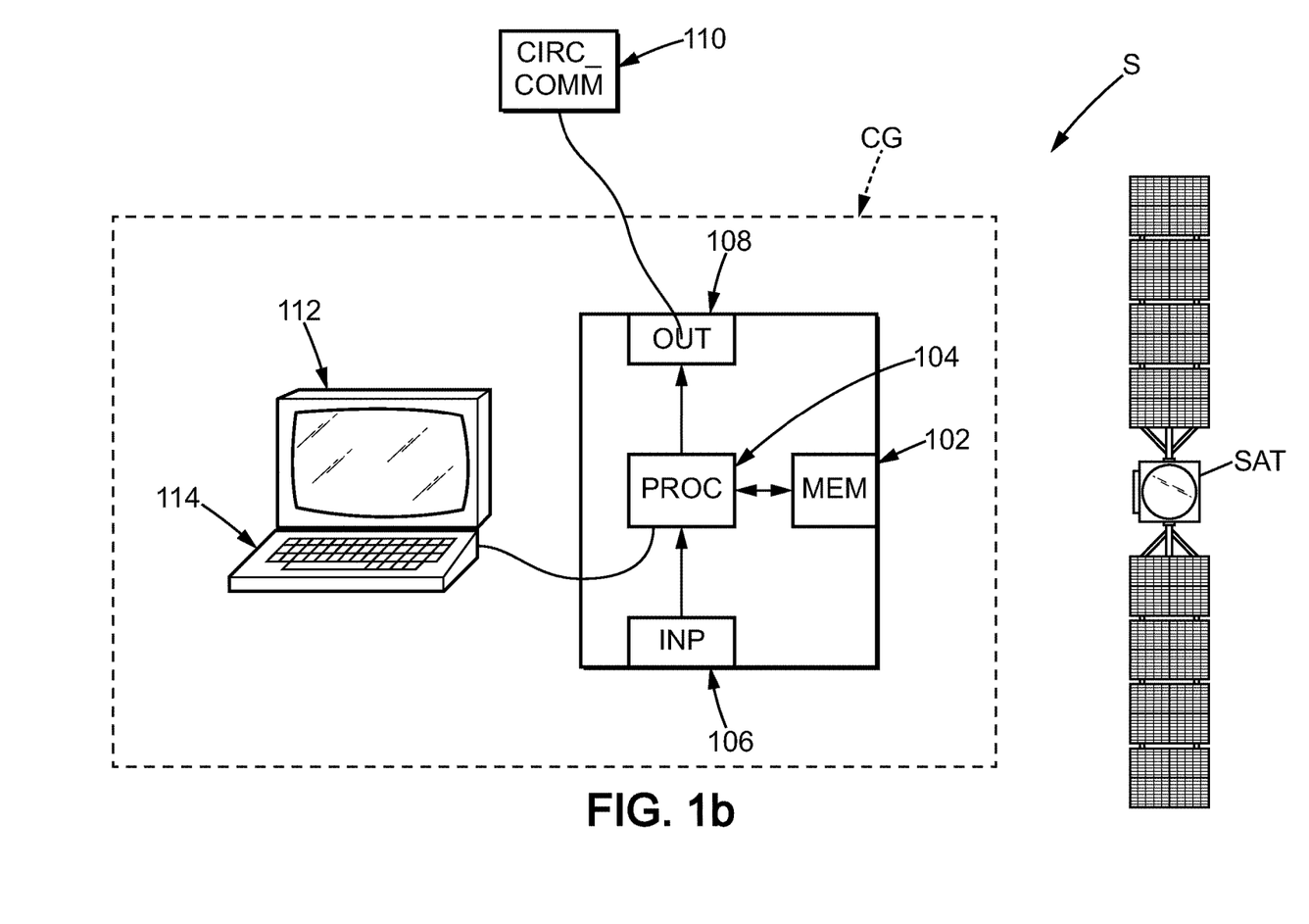

We first refer to FIG. 1b which represents the management center CG of the system S. The center CG may be a computer, comprising memory 102 for storing:

instructions for implementing the method, satellite data received, and temporary data for implementing the various steps of the method as described above and as detailed below.

The memory MEM may also store a database containing:

predefined volume fractions corresponding to volume fractions observed in known weather conditions, for sea surfaces having identified floating bodies; and/or a bathymetric mapping of the surveillance area.

The computer further comprises a data processing unit 104. This data processing unit may be a circuit, for example such as:

a processor capable of interpreting instructions in the form of a computer program, or a circuit board in which the steps of the inventive method are defined in the silicon, or a programmable chip such as an FPGA (Field-programmable Gate Array).

This computer has an input interface 106 for receiving satellite data, and an output interface 108 for supplying alerts to a remote device 110 upon detection of a floating layer. Finally, the computer may include a screen 112 and a keyboard 114, for easy user interaction. The keyboard is of course optional, for example in the context of a tablet computer with touchpad.

The input interface 106 may receive hydrodynamic models from sources of information about the hydrodynamic conditions of the surveillance area, such as a server of an ocean monitoring center.

Typically, the remote device 110 may be a monitoring platform of a power plant or a client terminal capable of receiving alerts from the center GC via the interface 108. To this end, the device 110 may comprise a communication interface capable of receiving data from the center CG and a data processing unit for interpreting them. Alerts received by the remote device 110 can thus be used by said device to anticipate potential clogging and/or blockages. As an illustrative example, a user can receive telephone alerts for a power plant he or she oversees. The user can then implement preventive actions to forestall the possibility of blockages (and thus the need to shut down the production of power by the plant). Various services may further be offered to users according to various possible interpretations of alerts by the remote device 110.

In addition, the interface 106 may receive qualitative and quantitative data concerning weather conditions and winds. These data may, for example, come from an anemometer placed at or near the management center CG, or at least close to the region of the sea to be monitored and to the thermal power station. This data can be taken into account to refine the determination of the volume fraction corresponding to the altimetric measurements sent by the satellite.

Figure 2:
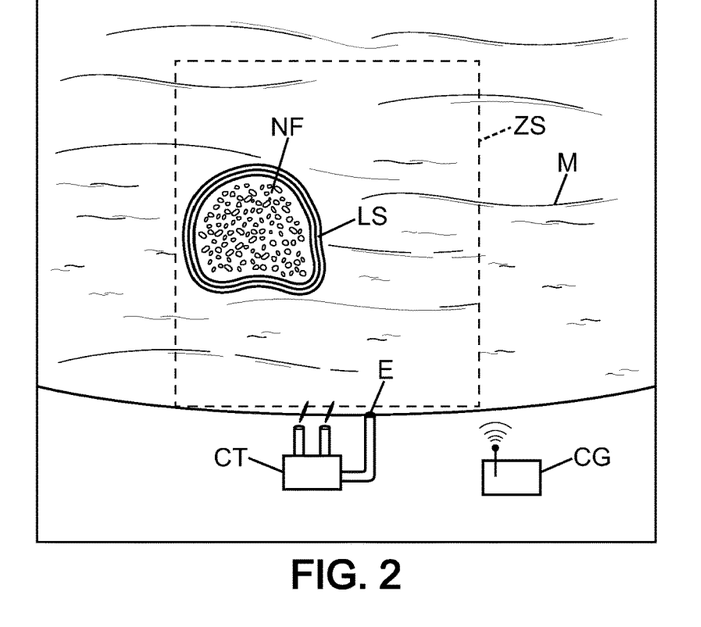
FIG. 2 illustrates an exemplary satellite image of a coastline where a thermal power plant is installed, with a floating layer close to the plant.

FIG. 2 shows an exemplary satellite image of a coastline where a thermal power station CT has been installed. The area monitored by the satellite is the surveillance area ZS, located close to the intake E to the cooling system of the plant CT.

Using satellite measurements received by the management center CG, it is possible to detect altimetric variations at the surface of the sea M. A floating layer NF is currently present on the sea M. In this example, the layer NF is a cluster of jellyfish.

At the edges of the layer NF, the swell of the sea M changes abruptly. The sudden variations in the swell at the edges form the distinctive boundaries LS.

Figure 3:
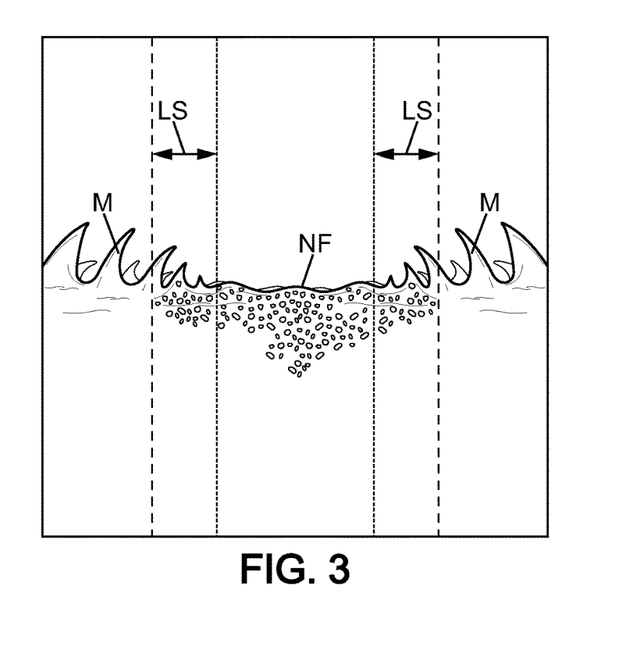
FIG. 3 is an exemplary sectional view of the swell of the sea surface at the floating layer.

In FIG. 3, an exemplary cross-sectional view of the swell is represented on the surface of the sea M at the floating layer NF. The swell of the sea M has a regular wavelength and amplitude. The swell in the layer NF is different because of the presence of the floating bodies (jellyfish). In this example, there is almost no swell in the layer NF. The swell of the sea is rapidly dampened at the edges of the layer NC, forming distinctive boundaries which separate the swell profile of the sea from the swell profile of the layer.

The distinctive boundaries LS are areas at the edges of the layers NF where a more pronounced damping of the swell is observed. This distinction is caused by a greater local viscosity of the fluid due to the presence of floating bodies (for example jellyfish or other).

Figure 4:
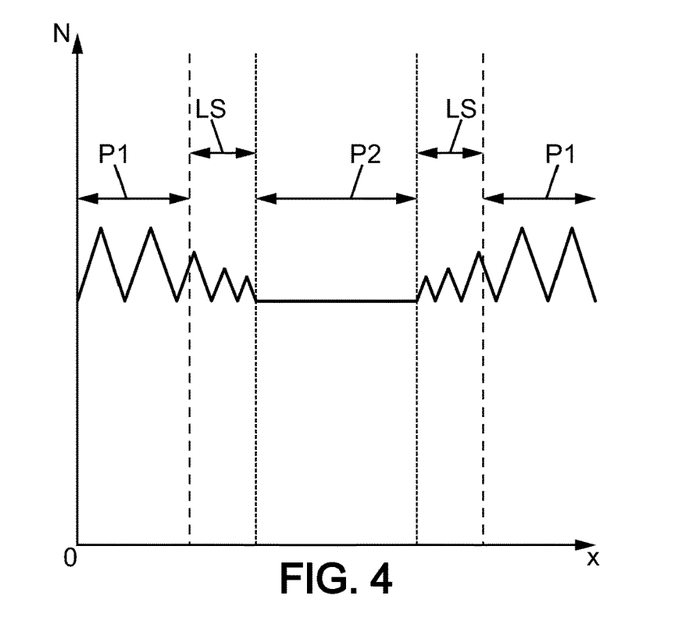
FIG. 4 is an exemplary graphical representation of the levels of measurements obtained by the satellite at the floating layer located in the surveillance area.

In FIG. 4, a graph shows the variation in the detection level N of the measurements as a function of the position x of the measurements in the surveillance area ZS. Satellite measurements of the returned radar signal have variations in the detection levels corresponding to the altimetric variations at the water surface.

From the satellite measurements, the management center CG can recognize:

a first swell profile and a second swell profile for sets of measurements P1 and P2 having levels respectively corresponding to the same swell characteristics (same wavelength and same amplitude); and distinctive boundaries LS that correspond to strong localized variations in the satellite measurement levels.

Using the measurements made, a map of the mechanical properties of the swell is obtained for the surveillance area ZS.

Figure 5:
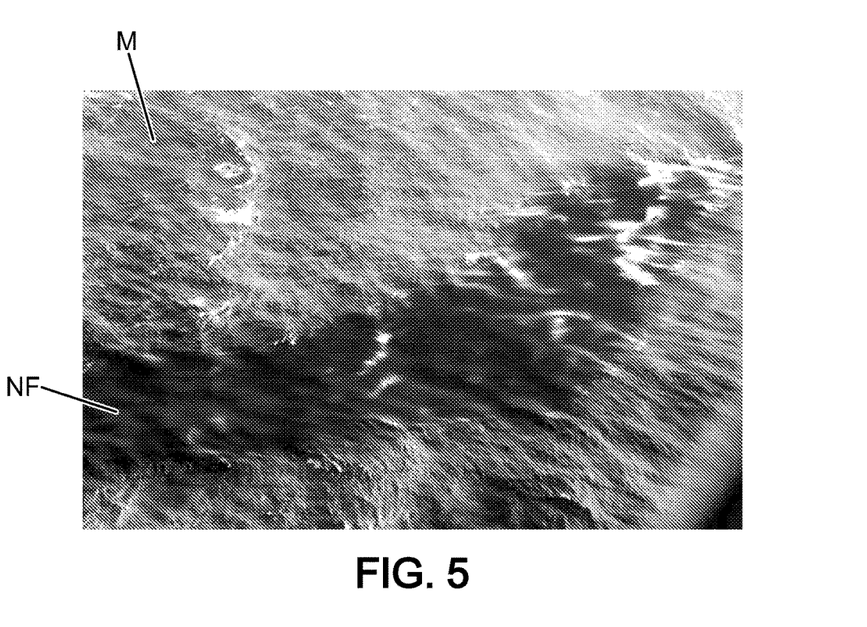
FIG. 5 is an illustrative example of a floating layer of crude oil as seen from the sky.

We now refer to FIG. 5 in which a floating layer NF of crude oil is illustrated.

The layer of oil formed on the surface of the sea M affects the viscosity and surface tension, thereby altering the apparent roughness at the water surface.

The layer NF has a lower roughness than the sea. The swell profiles can be differentiated by their respective roughnesses, which differ.

Figure 6:
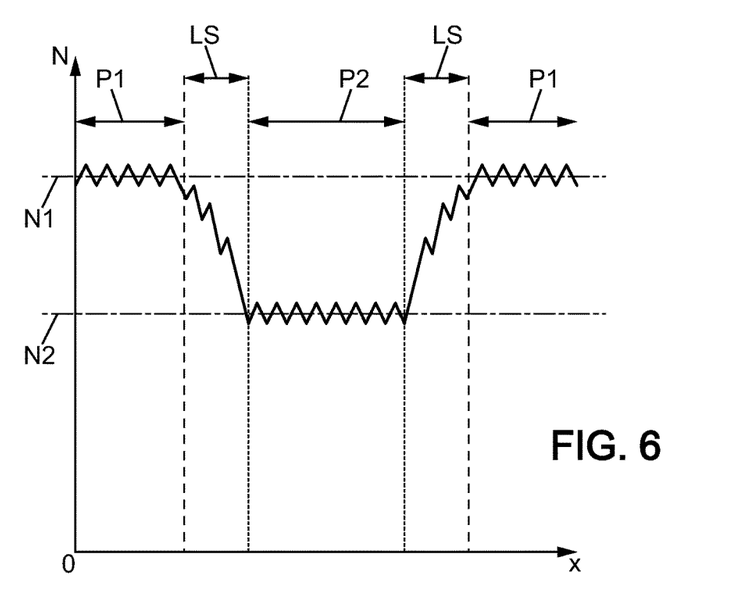
FIG. 6 is an example of a graphical representation of the levels of measurements obtained by the satellite at the floating layer of crude oil located in the surveillance area.

In FIG. 6, a graph is represented which also shows, as in FIG. 4, the variation in the detection level N of the measurements as a function of the position x of the measurements in the surveillance area ZS.

The variations in measurement levels oscillate between a first level N1 and a second level N2, depending on the location of the measurements in the area ZS. The first and second levels correspond to different roughnesses (surface wavelets of the swell) of the sea surface. As mentioned above, areas of high roughness return a strong radar echo to the satellite, and conversely, areas of low roughness reflect very little radar signal to the satellite.

The swell profiles of the sea M and of the layer NF can thus be recognized via:
- a first set of measurements P1 substantially at the first level N1, corresponding to the swell profile of the sea M, and
- a second set of measurements P2 substantially at the second level N2, corresponding to the swell profile of the layer NF.

We now refer to FIG. 7, which illustrates a flowchart composed of an exemplary sequence of steps in the method for detecting a floating layer.

In step 700, the dimensions and location of the surveillance area ZS are defined (DEF (ZS)). The dimensions of the surveillance area may be determined based on parameters among the following:
- speeds of the ocean currents;
- a tidal coefficient;
- weather conditions;
- a desired surveillance frequency; and
- frequency at which the satellite passes over the surveillance area.

The surveillance area is located above a site of interest such as power plant CT or at least at the edge of this site (for example at sea, off the coast near the power plant CT).

In a step 702, the satellite SAT transmits radar signals to the sea surface of the surveillance area ZS and measures the level of the return signal (MES). Satellite measurements by radar allow obtaining a real-time spatial mapping of the sea surface (geometry of the waves). The raw information obtained from the satellite is the altimetry of the sea surface in the surveillance area. The resolution of this mapping is directly related to satellite performance. The choice of satellites used may consider as a parameter the desired resolution for the analysis of swell characteristics (amplitude and wavelength of the waves).

In a step 704, the management center CG receives the satellite data concerning the measurements and interprets them so as to recognize at least one swell profile P of the sea surface (REC(P)). A swell profile may be recognized for a set of measurements corresponding to similar swell characteristics.

To better differentiate between the different swell profiles that are present, rapid transition areas are identified in the surveillance area. These rapid transition areas form the distinctive boundaries LS of the swell profiles and correspond to pronounced localized variations in the satellite measurement levels. The identified distinctive boundaries define the transition between two different swell profiles.

In addition, to ensure that the areas of rapid transition are not those inherent to shallow seas in the surveillance area, the recognized distinctive boundaries may be compared to a bathymetric mapping of the surveillance area. Cross-checking with the bathymetric mapping allows identifying and isolating changes to the swell caused by bathymetric refraction.

This step of identifying distinctive boundaries from changes in the swell may be performed on the basis of visual examination, by an operator, of the altimetric mapping obtained using the satellite measurements for the surveillance area. This step may also be carried out by automatic processing that identifies the distinctive boundaries on the basis of the mechanical properties of the swell exceeding a spatial gradient criterion.

Swell profile recognition may be carried out by identifying:
- a set of measurements of substantially the same level, the set of measurements being defined at least in part by the recognized distinctive boundaries, or
- a set of measurements for which the level varies by a same wavelength and a same amplitude, the set of measurements being defined at least in part by the recognized distinctive boundaries.

In a step 706, the fluid properties PF corresponding to the swell profiles are identified (ID(PF)).

When at least two swell profiles correspond to sets of measurements of substantially the same levels respectively, the first and second levels can be compared. Typically, in the example of FIG. 6, the first swell profile (corresponding to a set of measurements P1) is identified as the set of measurements of substantially the first level N1, and the second swell profile (corresponding to a set of measurements P2) is identified as the set of measurements of substantially the second level N2.

Depending on the comparison of the levels, the first or second swell profile corresponding to the lower of the compared levels can be associated with fluid properties PF of a sea surface that includes undesirable elements for the site of interest. The other among the first and second profiles (corresponding to the higher of the levels) can be associated with fluid properties typically observed for an ocean surface in the open sea.

When the swell profile corresponds to a set of measurements in which the level varies by a same wavelength and a same amplitude, the fluid properties of the at least one recognized swell profile are identified by:
- determining a volume fraction as a function of:
  - a damping coefficient of amplitude a of the swell at the distinctive boundaries,
  - a number of waves k at the distinctive boundaries, determined from the wavelength of the recognized swell profile,
- identifying the fraction among predefined volume fractions that is closest to the determined volume fraction, the predefined volume fractions being associated with predetermined fluid properties; and
- associating the recognized swell profile with the predetermined fluid properties of the predefined volume fraction identified as being closest to the determined volume fraction.

The approach consists of linking the variations in the mechanical properties of the swell (swell damping) to the fluid properties of the sea surface, and for this purpose it may use fluid mechanics equations that are based on:
- the laws of conservation of energy (in the form of the relation between wave damping at the distinctive boundaries and fluid viscosity),
- an empirical relation, for mixtures in suspension, between the apparent viscosity and the concentration of solid particles.

As for the laws of conservation of energy, swell damping α by viscous dissipation can be determined using the following exponential law:

$$A = A_0 e^{-\alpha x}$$

This relation allows calculating wave damping α as a function of the amplitude of the waves detected for the recognized swell profile, a reference amplitude $A_0$, and the width x of the distinctive boundaries LS.

In practice, the damping coefficient $\alpha$ is thus obtained by graphically measuring the damping of wave amplitude on the mapping of altimetric measurements.

From the damping $\alpha$ calculated at the separating boundaries, the viscosity $\mu$ of the swell profile can be calculated using a relation for gravity waves of the type:

$$\mu = \rho\omega\alpha(4k^3)^{-1}$$

In this relation, k is the number of swells k detected at the distinctive boundaries LS, $\alpha$ corresponds to the damping calculated using the above relation, $\rho$ is the density of the fluid, and $\omega$ corresponds to the angular frequency of the swell.

For some swell types (in particular low amplitude and low wavelength), the effects of surface tension are not insignificant and must be taken into account. According to another possible embodiment, the viscosity $\mu$ can then be calculated based on the effects of surface tension $\sigma$, as follows:

$$\mu = \left(\frac{\alpha\rho}{2k^2}\right)\left(\frac{g + 3\frac{\sigma k^2}{\rho}}{2\left(kg + \frac{\sigma k^3}{\rho}\right)^{1/2}}\right)$$

The viscosity $\mu$ of the sea surface corresponding to the swell profile can be used to characterize the viscosity of the mixture in suspension at the surface of seawater.

To this end, one can use the case of a mixture in suspension with a density between the fluid (seawater) and the solid particles (marine organisms) that is considered to be constant. The viscosity of such a mixture in suspension (seawater/marine organisms) can be defined by:

$$\mu_s = \mu_r * \mu_l$$

In this relation, $\mu_s$ corresponds to the viscosity of the mixture, $\mu_l$ corresponds to the viscosity of the seawater, and $\mu_r$ is a relative viscosity (dimensionless).

There are several empirical models for defining $\mu_r$ as a function of the volume fraction $\varphi$ of solid particles. For example, the Thomas empirical model is as follows:

$$\mu_r = 1 + 2.5\varphi + 10.05\ \varphi^2 + Ae^{\beta\varphi}, \text{ where } A = 0.00273 \text{ and } \beta = 16.6.$$

There is also the Kitano model in which:

$$\mu_r = \left(1 - \left(\frac{\phi}{A}\right)\right)^{-2},$$

where A=0.68 for spherical particles.

Other similar models may also be used, such as the Krieger-Dougherty empirical model.

From the relative viscosity $\mu_r$, one can thus determine the volume fraction $\varphi$ of the mixture at the sea surface having the recognized swell profile. This volume fraction describes the fluid properties of the recognized profile.

In addition, qualitative and quantitative data on the winds and weather may be taken into account in order to refine the volume fraction determination.

The determined volume fraction may be compared to a database of predefined volume fractions.

As mentioned above, the fluid properties of the determined volume fraction $\varphi$ are considered as corresponding to the predetermined fluid properties of the most similar fraction among the predefined volume fractions.

Using the fluid properties PF identified for the swell profile P, step 708 verifies whether or not the swell profile has fluid properties that correspond to the fluid properties of a sea surface comprising undesirable elements EP for the plant CT (PF⇔EP?).

When the fluid properties correspond to a floating layer containing floating bodies (Y arrow exiting step 708), then an alert is issued in step 710 (ALERT), for example to the remote device 110 mentioned above.

This alert provides warning of the possibility of drum screen clogging for example. It is then possible to implement preventive measures to avoid such obstruction.

Otherwise, as indicated by the arrow N exiting step 708, the fluid properties do not correspond to a floating layer, or at least not to a floating layer posing a threat to the plant CT. The method then ends in step 712 (END) and can be repeated to obtain new measurements and recheck for the presence of a threatening floating layer in the surveillance area.

In addition, in order to overcome the temporally discontinuous nature of information from satellites (which is dependent on how frequently a satellite passes over the area of interest), the detection of a layer of marine organisms may be coupled with digital hydrodynamic models. The principle consists of injecting detected floating layers into the hydrodynamic models, and modeling the drift of these layers over the following days based on ocean currents. Weather forecasts may also be considered, in particular to include the influence of winds on the ocean currents.

This allows estimating the future movement of a swell profile corresponding to a floating layer posing a threat to a nuclear power plant, which allows taking pre-emptive measures for example to protect the cooling system of the plant.

The database of predefined volume fractions may be constructed from:
  a history of prior clogging events at the plant CT,
  a known volume fraction for identified floating bodies,
  ranges of damping coefficients or viscosities that are typically observed for the concentrations of clusters of clogging organisms or other bodies,
  behaviors specific to biological species,
  characteristics of floating bodies on an immiscible free surface,
  or other.

The database may be in the form of a multidimensional table that includes volume fractions of floating bodies classified by time of year, water temperature, etc.

The inclusion of behaviors specific to biological species helps to distinguish between species in the identification of fluid properties. For example, the water column of some jellyfish species changes with the light levels, resulting in a detectability that is dependent on the time of day (fluid properties evolve with the behavior of the floating organisms over the course of a day).

This database allows refining the empirical relationship between apparent viscosity and particle content of a mixture in suspension, and assigning specific empirical coefficients to each type of marine organism (by types of algae, types of jellyfish, etc.).

It is therefore understood that the invention is based on the principle that sea waves can be modified/damped when they encounter a cluster of marine organisms (for example jellyfish, algae, etc.).

Detection of a floating layer allows triggering an early warning when one or more clusters of marine organisms or slicks of crude oil are approaching a nuclear power plant (and more particularly the filtering drum screens of the cooling system).

The proposed detection method and system advantageously:

offer extensive coverage spatially, and are operational day and night, regardless of cloud cover.

Potentially, the proposed detection method and system may also allow detection of vessels releasing oil at sea, particularly at night.

The invention has been described with reference to particular embodiments, which are non-limiting. The invention is of course not limited to the embodiment described by way of example, and extends to other variants. For example, the detection method and system may also be implemented for facilities such as offshore wind farms, to verify their accessibility during maintenance operations.

The invention claimed is:

1. A method for detecting a floating layer on a surveillance area of a sea surface, a site of interest being located in or at the edge of the surveillance area, the method comprising:
   a) satellite measurements of a returned radar signal, the radar signal being transmitted by a satellite toward the sea surface of the surveillance area;
   b) recognition of a swell profile of the sea surface, based on the satellite measurements;
   c) identification of fluid properties corresponding to the recognized swell profile; and
   d) emission of a warning when the fluid properties identified for one of the recognized profiles correspond to a sea surface comprising elements belonging to a predefined set of elements that are undesirable for the site of interest,
   wherein, in b), a boundary of the swell profile is further recognized in the surveillance area, the boundary corresponding to localized variations in levels of the satellite measurements greater than a predefined variation threshold;
   wherein the recognized swell profile corresponds to a set of measurements among the satellite measurements whose level varies according to a same wavelength and a same amplitude, the set of measurements being delimited at least in part based on the recognized boundary; and
   wherein, in c), the fluid properties of the recognized swell profile are identified by:
   determining a volume fraction as a function of:
      a damping coefficient of swell amplitude at the boundary,
      a number of waves at the boundary, determined from the wavelength of the recognized swell profile,
   identifying a first volume fraction among predefined volume fractions that is closest to the determined volume fraction, the predefined volume fractions being associated with predetermined fluid properties; and
   associating the recognized swell profile with the predetermined fluid properties of the identified first volume fraction.

2. The method according to claim 1, wherein dimensions of the surveillance area are based on at least one parameter among:
   speeds of the ocean currents;
   a tidal coefficient;
   weather conditions;
   a predetermined surveillance frequency; and
   frequency at which the satellite passes over the surveillance area.

3. The method according to claim 1, wherein the recognized swell profile corresponds to a subset of measurements among the set of measurements having substantially a same level.

4. The method according to claim 3, wherein, in the surveillance area:
   a first swell profile is recognized from a set of measurements among the satellite measurements of substantially a same first level,
   a second swell profile is recognized from a set of measurements among the satellite measurements of substantially a same second level,
   wherein the first level and the second level are compared, and
   wherein the swell profile corresponding to a lower of the compared levels among the first swell profile and the second swell profile is associated with the fluid properties of a sea surface having elements belonging to a predefined set of elements that are undesirable for the site of interest.

5. The method according to claim 1, wherein the volume fraction is also a function of a surface tension of the sea surface corresponding to the recognized swell profile.

6. The method according to claim 1, wherein the predefined volume fractions correspond to volume fractions observed, in known weather conditions, for sea surfaces having identified floating bodies.

7. The method according to claim 1, wherein the recognized boundary is compared to a bathymetric mapping of the surveillance area.

8. The method according to claim 1, further comprising:
   determining movement of the swell profile corresponding to a sea surface comprising elements belonging to a predefined set of elements that are undesirable for the site of interest, the movement determination being based on pre-established hydrodynamic models of the surveillance area or on hydrodynamic models from sources of information about the hydrodynamic conditions of the surveillance area.

9. A detection system for detecting a floating layer in a surveillance area of a sea surface, a site of interest being located in or at the edge of the surveillance area, the system comprising at least:
   a satellite configured to:
      transmit a radar signal toward the sea surface of the surveillance area;
      measure a return signal of the transmitted radar signal;
      communicate data concerning the measurement levels of the measured return signals;
   a management unit comprising:
      a communication interface configured to receive data communicated by the satellite, and
      a data processing unit configured to implement a method for detecting a floating layer on a surveillance area of a sea surface, a site of interest being located in or at the edge of the surveillance area, the method comprising:
         a) satellite measurements of a returned radar signal, the radar signal being transmitted by a satellite toward the sea surface of the surveillance area;
         b) recognition of a swell profile of the sea surface, based on the satellite measurements;
         c) identification of fluid properties corresponding to the recognized swell profile; and
         d) emission of a warning when the fluid properties identified for one of the recognized profiles correspond to a sea surface comprising elements belonging to a predefined list of elements that are undesirable for the site of interest;

wherein, in b), a boundary of the swell profile is further recognized in the surveillance area, the boundary corresponding to localized variations in levels of the satellite measurements greater than a predefined variation threshold;

wherein the recognized swell profile corresponds to a set of measurements among the satellite measurements whose level varies according to a same wavelength and a same amplitude, the set of measurements being delimited at least in part by the recognized boundary; and wherein, in c), the fluid properties of the recognized swell profile are identified by:

determining a volume fraction as a function of:
- a damping coefficient of swell amplitude at the boundary,
- a number of waves at the boundary, determined from the wavelength of the recognized swell profile, identifying a first volume fraction among predefined volume fractions that is closest to the determined volume fraction, the predefined volume fractions being associated with predetermined fluid properties; and associating the recognized swell profile with the predetermined fluid properties of the identified first volume fraction.

10. The detection system according to claim 9, further comprising a database configured for storing data relating to:
- predefined volume fractions corresponding to volume fractions observed, in known weather conditions, for sea surfaces having identified floating bodies; and/or
- a bathymetric mapping of the surveillance area.

11. A non-transitory computer readable storage medium, having stored thereon a computer program comprising program instructions, the computer program being loadable into a data-processing unit and adapted to cause the data-processing unit to carry out a method for detecting a floating layer on a surveillance area of a sea surface, a site of interest being located in or at the edge of the surveillance area, the method comprising:

a) satellite measurements of a returned radar signal, the radar signal being transmitted by a satellite toward the sea surface of the surveillance area;

b) recognition of a swell profile of the sea surface, based on the satellite measurements;

c) identification of fluid properties corresponding to the recognized swell profile; and d) emission of a warning when the fluid properties identified for one of the recognized profiles correspond to a sea surface comprising elements belonging to a predefined set of elements that are undesirable for the site of interest;

wherein, in b), a boundary of the swell profile is further recognized in the surveillance area, the boundary corresponding to localized variations in levels of the satellite measurements greater than a predefined variation threshold;

wherein the recognized swell profile corresponds to a set of measurements among the satellite measurements whose level varies according to a same wavelength and a same amplitude, the set of measurements being delimited at least in part based on the recognized boundary; and wherein, in c), the fluid properties of the recognized swell profile are identified by:

determining a volume fraction as a function of:
- a damping coefficient of swell amplitude at the boundary,
- a number of waves at the boundary, determined from the wavelength of the recognized swell profile, identifying a first volume fraction among the predefined volume fractions that is closest to the determined volume fraction, the predefined volume fractions being associated with predetermined fluid properties; and associating the recognized swell profile with the predetermined fluid properties of the identified first volume fraction.

* * * * *